United States Patent [19]

Krasnicki et al.

[11] Patent Number: 4,676,229
[45] Date of Patent: Jun. 30, 1987

[54] BIOPSY CHANNEL FOR AN ENDOSCOPE

[75] Inventors: Edward J. Krasnicki, Skaneateles, N.Y.; Alan J. Hannibal, Fairview; Thomas R. Pherson, Erie, both of Pa.

[73] Assignee: Welch Allyn, Inc., Skaneateles Falls, N.Y.

[21] Appl. No.: 849,887

[22] Filed: Apr. 9, 1986

[51] Int. Cl.⁴ .............................................. A61B 1/00
[52] U.S. Cl. ........................................ 128/4; 604/282
[58] Field of Search ........................ 128/4, 3, 5, 6, 7; 604/280, 281, 282, 264, 265

[56] References Cited

U.S. PATENT DOCUMENTS

| | | | |
|---|---|---|---|
| Re. 31,289 | 6/1983 | Moore et al. | 128/6 |
| 3,946,727 | 3/1976 | Okada et al. | 128/4 |
| 3,960,143 | 6/1976 | Terada | 128/4 |
| 4,043,323 | 8/1977 | Komiya | 128/4 |
| 4,236,509 | 12/1980 | Takahashi et al. | 128/4 |
| 4,271,845 | 6/1981 | Chikashige et al. | 128/4 X |
| 4,279,245 | 7/1981 | Takagi et al. | 128/4 |
| 4,327,711 | 5/1982 | Takagi | 128/4 |
| 4,329,980 | 5/1982 | Terada | 128/4 |

Primary Examiner—William H. Grieb
Attorney, Agent, or Firm—Bruns and Wall

[57] ABSTRACT

A biopsy channel for use in an endoscope having a tubular substrate formed of a lubricious material that is wound with a high strength wire filament helically wound thereabout to provide spaces between the windings and a relatively softer elastomeric material blanketing the windings. A top coating also containing a lubricious material is placed over the filler material to provide a tubular structure that can be bent into a tight radius without collapsing.

25 Claims, 4 Drawing Figures

BIOPSY CHANNEL FOR AN ENDOSCOPE

BACKGROUND OF THE INVENTION

This invention relates to an improved biopsy channel for use in the insertion tube of an endoscope and, in particular, to a biopsy channel having improved lubricity, flexibility and strength.

Most biopsy channels found in the prior art are made of vinyl tubing. Vinyl possesses limited lubricity and it is therefore sometimes difficult to pass an instrument such as a biopsy forceps, through the channel when the insertion tube is required to negotiate a short radius, or tight, bend. The vinyl channel, being relatively stiff, further tends to buckle or flatten out along the length of the bend making it more difficult to pass an instrument through the restricted region. The wall of the vinyl channel is usually relatively thick to prevent the channel from collapsing when an internal vacuum is applied to the channel during certain medical procedures. The thick wall again adversely effects the channels ability to accommodate tight bends. A thick walled tube will not deform in specific areas in response to localized pressures normally exerted by rigid instruments, such as biopsy forceps or the like as the instrument is forced through a tight bend. Under certain conditions, the thick walled tube will in fact resist passage of the instrument through the restricted bend region.

Other types of elastomeric materials have been used in the fabrication of biopsy channels in an effort to overcome some of the difficulties associated with vinyl tubes. One such material is a commercially available substance marketed under the tradename Gortex. Although this material exhibits improved lubricity and flexibility, it is permeable and unless treated in some manner will pass air and fluids through its membrane-like channel wall. Similarly, this material lacks body strength and it must be reinforced in some way in order to preserve the integrity of the channel. A biopsy channel utilizing this type of material is disclosed in U.S. Pat. No. 4,279,245 to Takagi et al.

SUMMARY OF THE INVENTION

It is the primary object of the present invention to improve biopsy channels suitable for use within the insertion tube of an endoscope.

A further object of the present invention is to reduce the friction of a biopsy channel.

A still further object of the present invention is to provide a biopsy channel that is capable of deforming in localized areas in response to internal forces to permit rigid bodies to pass through tight bend regions.

Another object of the present invention is to increase the flexibility and strength of a biopsy channel so that the channel can be bent repeatably without damage.

Yet another object of the present invention is to provide a biopsy channel that can withstand internal pressures of 100 psi or more and a vacuum of 15 inches of mercury.

While a further object of the present invention is to provide a biopsy tube that can be bent into a radius of less than one inch without flattening out.

These and other objects of the present invention are attained by means of a biopsy channel having a thin hollow lubricious based substrate that is wound with a stiff small diameter mono-filament so that a space is provided between the windings and a flexible elastomeric filler material placed around the filament to fill the spaces. A thin lubricious top coating may be applied over the filler material to provide a low friction outer surface.

BRIEF DESCRIPTION OF THE DRAWINGS

For a better understanding of these and other objects of the present invention, reference is had to the following detailed description of the invention which is to be read in conjunction with the accompanying drawings, wherein.

DESCRIPTION OF THE INVENTION

Figure 1:
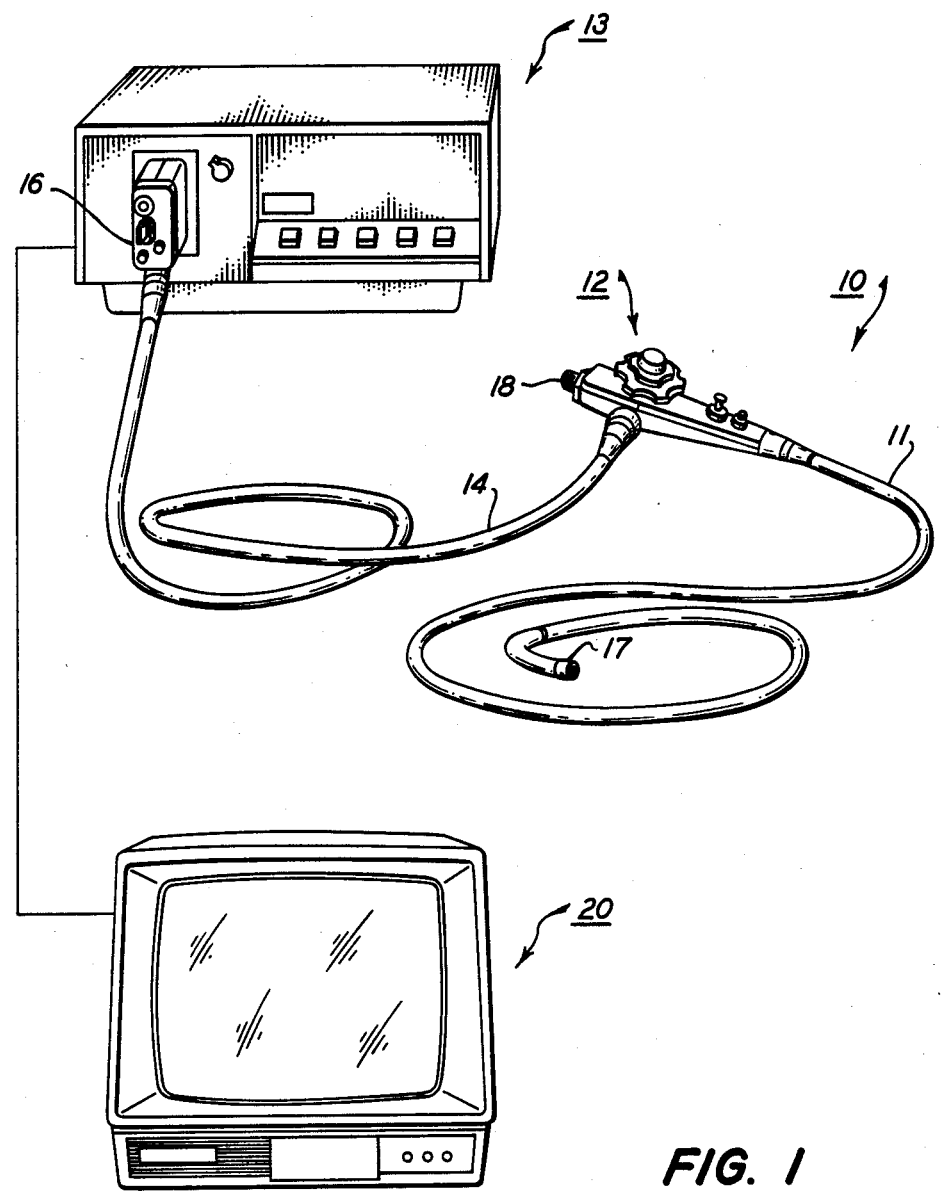
FIG. 1 illustrates a video-equipped endoscope that incorporates a biopsy channel embodying the teachings of the present invention.

Turning now to FIG. 1, there is shown an endoscope, generally referenced 10, that has a small video camera situated in the steering head 17 of the insertion tube 11. The camera includes a charge coupled device (CCD) that is capable of generating sufficient video information that is used to create a picture which is viewed by an examining physician upon a monitor 20. The proximal end of the insertion tube is attached to a control section 12 that houses various controls for steering the insertion tube and for carrying out related procedures. The control section is operationally joined to a video processor 13 by an umbilical cord 14 and a plug-in terminal 16. Video related signals are exchanged between the camera and the video processor via the umbilical cord and the insertion tube. Acquired image data in the target area of the camera is used to create a high resolution, full color picture of the target on the monitor screen. A biopsy port 18 is located at the back of the control section through which any one of many related instruments can be passed. The port opens into a biopsy channel that runs the full length of the insertion tube and which further opens into the target area through the distal end of the steering head 17. One such instrument that is continuously passed through the channel is a biopsy forceps from which the channel derives its name. A more thorough disclosure of a video equipped endoscope is founded in U.S. Pat. No. Re. 31,289, issued June 28, 1983 to Moore et al, and that disclosure is herein incorporated by reference to the extent necessary to understand the present invention.

Oftentimes, the insertion tube, and thus the biopsy channel, of an endoscope is required to transcend tight bends or turns as it is moved towards a desired target area. As previously pointed out, many of the biopsy channels found in the prior art tend to flatten out and stiffen in response to bend stresses. This, coupled with the fact that most channels lack lubricity, makes passage of an instrument through the bend area difficult.

As will become apparent from the disclosure below, the biopsy channel of the present invention is a thin walled device, which can be deflected or bent into a tight semi-circle without flattening or otherwise appreciably changing its internal geometry. The channel is formed of a highly lubricious material or materials so that an instrument inserted into the channel can freely pass through a tight bend region with little or no difficulty with a minimum amount of manipulation. The channel also has sufficient strength to withstand internal pressures up to 100 psi and a vacuum of 15 inches of mercury. Lastly, the present channel possesses a property sometimes referred to as "socking" that permits the channel to deform or stretch locally in response to internal pressures such as those exerted on the channel wall by an instrument as it moves through a tight bend to accommodate passage of the instrument. This ability to sock, in combination with the channels added lubricity and strength, provides the present device with an operational flexibility heretofore unknown in the art.

Figure 2:
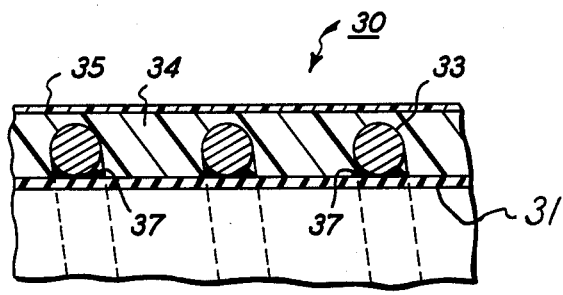
FIG. 2 is a partial enlarged view in section showing a first embodiment of a biopsy channel utilizing the teachings of the present invention.

Turning now to FIG. 2, there is shown a partial section, greatly enlarged, illustrating the construction of a first embodiment of the present invention. The biopsy channel 30 is tubular in cross-section and is constructed to permit the channel to bend easily into a tight radius while at the same time stretching locally in response to internal forces generated by a tool or instrument as it passes through the bend region. The inside diameter or opening of the channel is not critical to the invention, and generally ranges between 3.0 and 4.5 mm to accommodate various sized instruments depending upon the medical procedures involved.

Channel 30 includes an ultra-thin walled tubular substrate 31 formed of a highly lubricious material. Preferably, the liner is formed of a tetrafluorethylene (TFE) having a wall thickness of about 0.003 inches. As is well known, TFE is relatively stiff, having a modulus of elasticity of about 100,000 psi at 100% elongation, and therefore tends to buckle or collapse when bent in a tight radius. A support structure is built around the substrate which prevents it from collapsing when bent into a tight radius.

Initially, the outer surface of the tubular substrate is bonded and a thin mono-filament 33 is helically wound about the tube with the filament being in continuous contact with the tube along the entire length of the wrap. The filament reinforces the substrate and keeps it from collapsing when it is bent into a tight radius. The filament is formed from a single strand of wire having a modulus of elasticity of about $15 \times 10^6$ psi or greater. The filament is preferably formed of stainless steel although other materials having similar properties may also be used. The filament is strongly bonded to the outer surface of the tubular substrate using an adhesive 37 such as an epoxy cement having sufficient bond strength to hold the filament to the substrate as it is deformed into a tight radius.

The filament possesses three important parameters. The first, as noted above, is a high modulus of elasticity. The second is an optimum diameter that will minimize the wall thickness yet provide for the required liner support. Filaments having a diameter of between 0.004 and 0.016 have been found to work well in practice with a wire size of about 0.006 inches being preferred. It has been found generally that not much is gained in terms of performance when larger diameter filaments are employed. The last filament parameter involves the helical pitch of the windings. The term pitch, as herein used, refers to the axial distance between adjacent windings or, stated another way, the advance of the winding for each turn of the filament. For each complete turn about the substrate the filament should advance an axial distance about equal to 2.0 to 3.5 times the diameter of the filament. Accordingly, a space is provided between adjacent turns of the winding. In the case of a 0.006 diameter filament, a pitch of about 0.016 inches is preferred. The substrate may tend to pull away from the filament when a larger turn spacing is used. Too tight a winding on the other hand leads to excessive stiffness whereupon the channel loses its ability to negotiate tight bends.

The filament wound substrate is coated with a filler material 34 which fills the spaces between the filament turns. Preferably, the thickness of the filler coating is slightly greater than the filament diameter so that the filament is totally embedded or encapsulated within a filler blanket. The filler blanket provides a smooth outer coating over the filament and helps to strengthen the overall integrity of the structure. Preferably the filler blanket is fabricated of an elastomer material such as "C-flex", natural rubber and latex can be similarly employed. The filler material should have a modulus of elasticity of between 400 and 1000 psi at 100% elongation whereby the filler blanket has sufficient resiliency to deform as the channel is bent but yet provides sufficient cohesive strength so that the channel will not collapse during bending.

A highly lubricious outer coating 35 is placed over the filler blanket. The outer coating is formed of a material that is flexible yet stiffer than the blanket material. The coating thus provides low friction outer surface to the channel that can slide easily over any foreign objects that it might come in contact with, such as various functional components that are typically mounted inside the insertion tube of an endoscope. Preferably, the outer coating is formed of a blend of TFE and an elastomer material such as urethane having a modulus of elasticity of between 2000 and 3000 psi with the thickness of the coating being between 0.0005 and 0.001 inches. The coating blend may be placed over the filler blanket by use of either a dipping or spraying process. It has been found that a filler blanket having a modulus of elasticity of about 400 psi works well in combination with an outer coating utilizing a urethane having a modulus of elasticity of about 2400 psi at 100% elongation. Although urethane has been herein disclosed for use as a coating material, it should be clear to one skilled in the art that any type of elastomeric material having similar properties can be used in the practice of the present invention.

Figure 3:
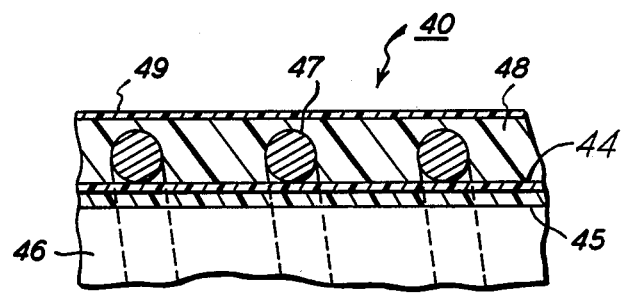
FIG. 3 is a partial enlarged view in section showing a second embodiment of the present invention.

As illustrated in FIG. 3, a second embodiment 40 of the present invention is disclosed that utilizes a tubular multi-layered substrate that exhibits slightly different properties than the single layer substrate described above. In order to furnish the desired lubricity to the inside surface of channels, the inner layer 45 of the substrate is formed of a blend containing between 30% and 70% TFE or FEP and an elastomer having a modulus of elasticity of between 2000 and 3000 psi at 100% elongation. Preferably, the blend is a 50/50 mixture of TFE and urethane. The TFE provides the desired lubricity to the inner layer while the urethane provides added strength and extends the ability of the substrate to elongate under strain. Both materials blend together well to form a smooth homogenious sleeve for the substrate.

An outer sleeve 44 is placed over the inner sleeve 45 of the substrate and is formed of an elastomer material having a modulus of elasticity of between 400 and 1000 psi at 100% elongation. Preferably, the sleeve 44 is fabricated from a urethane. The overall thickness of the multi-layered substrate is preferably about or less than 0.005 inches.

The multi-layered substrate is again wrapped with a wire filament 47 of the type described above in greater detail so that the filament is separated from the stiffer inner sleeve by the noted outer sleeve. Because of the nature of the multi-layered substrate, a softer wire filament having a modulus of elasticity as low as $1.0 \times 10^6$ psi can be utilized. Materials such as steel, nylon and polyesters can be used for this purpose. Similarly, bundles of fiber can be used as a filament wherein the fibers are held together in a rigid matrix using a suitable epoxy or polyester. The filament diameter again can range between 0.004 and 0.016 inches with diameters less than 0.010 inches being preferred in order to hold the overall diameter of the channel to a minimum.

The axial distance or pitch between the filament turns is between 2 and 3.5 times the filament diameter so that a uniform space is maintained between the turns. The spaces are filled by a flexible elastomeric blanket 48 that is formed of the same material as the outer sleeve 44 of the tubular substrate. The thickness of the blanket is preferably slightly greater than the filament diameter and the blanket thus enclosed the wire along its entire length. The blanket and the outer sleeve of the substrate thus combine to encapsulate the filament in a shell that is softer than the inner sleeve of the substrate. The outside of the blanket is coated with a blend of TFE and an elastomer having an elasticity of between 2000 and 3000 psi at 100% elongation. A 50/50 blend of TFE and urethane applied to the blanket to a thickness of 0.0005 and 0.001 inches works well in practice. The outer coating 49 may be formed by wrapping the blanket with commercially available tape.

Figure 4:
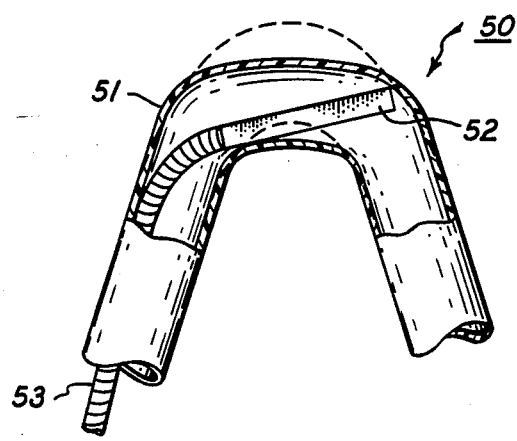
FIG. 4 is a partial side elevation of a biopsy channel incorporating the teachings of the present invention showing a biopsy forceps moving through a tight bend region and the channel deforming in a localized area on internal stress produced by the instrument.

Turning now to FIG. 4, there is shown a biopsy channel 50 that embodies the teachings of the present invention. The channel is illustrated transcending a relatively tight bend and thus is forced into a small radius loop shown in dotted outline at 51 which normally would restrict the channel opening and thus prevent passage of a biopsy forceps 52 of any other similar tool. The channel, because of its construction, has the ability to pass a tool through this region because of its unique property referred to as socking. This property permits the channel to stretch at the bend without collapsing.

This socking effect is shown slightly exaggerated in FIG. 4 by the solid lines portion of the drawing. The forceps 52 is carried at the distal end of a flexible insertion wire 53. As the forceps moves through the bend region, the front of the instrument rides in contact against the inside of the channel opening 54. The trailing part of the tool and the insertion wire push the end of the tool along the opening wall in the bend region. Normally, this action would cause the tube to bulge or dimple outwardly at the contact point causing the tool to get stuck in the tube. Pushing harder on the tool only magnifies the situation and leads to a greater restriction of the channel opening in the bend region. In the present channel, the substrate is not only lubricated but also reinforced so that it will not dimple or deform outwardly when the distal end of the tool encounters the substrate wall.

As illustrated in FIG. 4, rather than deforming or collapsing under the tool pressure, the channel will change the geometry of the bend slightly so that the top of the bend flattens out and the distance between the sides of the loop widens. Because of the flexible nature of the channel structure, the tube is able to stretch axially along the bend to accommodate the tool as shown without collapsing the channel opening. Accordingly, as the tool moves through the bend region, this slight change in geometry and the stretching effect follows the tool around the bend to produce the socking effect.

While the invention has been described in detail with respect to a preferred embodiment, it should be understood that this invention is not limited to that embodiment, and that many modifications and variations thereof could be effected by those skilled in the art without departure from the scope and spirit of this invention, as defined in the appended claims.

We claim:

1. A biopsy channel for mounting within the insertion tube of an endoscope that includes a thin wall tubular substrate formed of a lubricious material that allows an instrument to pass freely therethrough, a high strength filament wound about the outer surface of the substrate, the pitch of the winding being greater than the diameter of the filament to provide a space between the windings, a filler material forming a blanket about the windings to fill the spaces therebetween, said filler material being a flexible elastomeric material having a modulus of elasticity that is less than that of the substrate.

2. The biopsy channel of claim 1 wherein the filament has a modulus of elasticity at or above $15 \times 10^6$ psi.

3. The biopsy channel of claim 2 wherein the tube is formed of tetrafluorethylene (TFE) member having a wall thickness of about 0.003 inches and the filament is a steel wire having a diameter of between 0.004 and 0.010 inches.

4. The biopsy channel of claim 1 wherein the filler material is a urethane material having a modulus of elasticity of between 400 and 1000 psi at 100% elongation.

5. The biopsy channel of claim 1 that further includes a thin outer coating of a lubricious material that is placed over the filler material.

6. The biopsy channel of claim 5 wherein the outer coating is tetrafluorethylene (TFE) and has a wall thickness of between 0.0005 and 0.001 inches.

7. The biopsy channel of claim 5 wherein the outer coating is a blend of TFE and a second flexible elastomeric material having a modulus of elasticity of between 2000 and 3000 psi at 100% elongation.

8. The biopsy channel of claim 7 wherein the second elastomeric material is urethane that makes up about 50% of the outer coating by weight.

9. The biopsy channel of claim 1 wherein the axial distance between filament windings is between 2 and 3.5 times the diameter of the filament.

10. The biopsy channel of claim 1 that further includes adhesive means for bonding the filament to the substrate.

11. The biopsy channel of claim 4 wherein the thickness of the filler material is slightly greater than the diameter of the filament whereby the filament is embedded beneath the surface of the filler material.

12. The biopsy channel of claim 1 wherein the filament is metal.

13. A biopsy channel for mounting within the insertion tube of an endoscope that includes
a multi-layered substrate having a tubular inner sleeve formed of lubricious material having a modulus of elasticity of between 2000 and 3000 psi at 100% elongation, and an outer sleeve formed of a flexible elastomeric material having a modulus of elasticity that is less than that of the inner sleeve, a high strength filament helically wound about the substrate that has a pitch that is greater than the diameter of the filament to provide a space between the adjacent windings, and a flexible elastomeric filler material placed over the filament windings to fill the spaces therebetween having a modulus of elasticity that is less than that of the inner sleeve.

14. The biopsy channel of claim 13 wherein the inner sleeve includes a blend of tetrafluorethylene and a flexible elastomer.

15. The biopsy channel of claim 13 wherein the substrate has an overall wall thickness equal to or less than 0.005 inches and the filament has a diameter of between 0.004 and 0.016 inches.

16. The biopsy channel of claim 13 that further includes an outer coating placed over the filler material that is formed of a flexible lubricious material.

17. The biopsy channel of claim 15 wherein the outer coating is tetrafluorethylene having a thickness of between 0.0005 and 0.001 inches.

18. The biopsy channel of claim 15 wherein the top coating is a blend of tetrafluorethylene and a urethane having a modulus of elasticity of between 2000 and 3000 psi AT 100% elongation, said outer coating being between 0.0005 and 0.001 inches thick.

19. The biopsy channel of claim 13 wherein the filament has a modulus of elasticity of at or about $10 \times 10^6$ psi.

20. The biopsy channel of claim 18 wherein the filament is selected from a material consisting of steel, stainless steel, nylon and polyester.

21. The biopsy channel of claim 15 wherein the axial distance between filament windings is between 2 and 3.5 times the diameter of the filament.

22. The biopsy channel of claim 20 wherein the filler material has a modulus of elasticity of between 400 and 1000 psi at 100% elongation.

23. The biopsy channel of claim 15 wherein the thickness of the filler material is slightly greater than the diameter of the filament so that the filament is embedded beneath the surface of the filler material.

24. The biopsy channel of claim 15 wherein the outer sleeve of the substrate is formed of a urethane material having a modulus of elasticity of about 400 psi at 100% elongation.

25. The biopsy channel of claim 23 wherein the filler is a also formed of the same material as the outer sleeve whereby the filament is completely embedded in said material.

* * * * *